US006768034B2

(12) United States Patent
Fung et al.

(10) Patent No.: US 6,768,034 B2
(45) Date of Patent: Jul. 27, 2004

(54) CATALYTIC PRODUCTION OF OLEFINS AT HIGH METHANOL PARTIAL PRESSURES

(75) Inventors: Shun C. Fung, Bridgewater, NJ (US); Keith H. Kuechler, Friendswood, TX (US); Jeffrey S. Smith, Seabrook, TX (US); Nicolas P. Coute, Houston, TX (US); Stephen N. Vaughn, Kingwood, TX (US); Chunshe Cao, Washington, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 31 days.

(21) Appl. No.: 10/339,044

(22) Filed: Jan. 9, 2003

(65) Prior Publication Data

US 2003/0109765 A1 Jun. 12, 2003

Related U.S. Application Data

(63) Continuation of application No. 09/506,843, filed on Feb. 18, 2000, now Pat. No. 6,531,639.

(51) Int. Cl.$^7$ ............................................... C07C 1/20

(52) U.S. Cl. ....................... 585/329; 585/326; 585/327; 585/638; 585/639; 585/640

(58) Field of Search ................................ 585/638, 639, 585/640, 326, 327, 329

(56) References Cited

U.S. PATENT DOCUMENTS

| | | | |
|---|---|---|---|
| 3,258,455 A | 6/1966 | Natta et al. ................. 260/93.7 |
| 3,305,538 A | 2/1967 | Natta et al. ................. 260/93.7 |
| 3,364,190 A | 1/1968 | Emrick ....................... 260/93.7 |
| 3,645,992 A | 2/1972 | Elston ...................... 260/80.78 |
| 3,911,041 A | 10/1975 | Kaeding et al. ............. 260/682 |
| 4,076,698 A | 2/1978 | Anderson et al. ......... 526/348.6 |
| 4,163,721 A | 8/1979 | Lobdell ....................... 210/232 |
| 4,243,691 A | 1/1981 | Mohlenkamp, Jr et al. . 426/649 |
| 4,302,565 A | 11/1981 | Goeke et al. ................... 526/88 |
| 4,310,440 A | 1/1982 | Wilson et al. ............... 252/435 |
| 4,440,871 A | 4/1984 | Lok et al. .................... 502/214 |
| 4,499,327 A | 2/1985 | Kaiser ......................... 585/640 |
| 4,500,651 A | 2/1985 | Lok et al. .................... 502/208 |
| 4,524,234 A | 6/1985 | Kaiser ......................... 585/638 |
| 4,527,001 A | 7/1985 | Kaiser ......................... 585/640 |
| 4,554,143 A | 11/1985 | Messina et al. ............. 423/306 |
| 4,567,029 A | 1/1986 | Wilson et al. ............... 423/306 |
| 4,613,721 A | 9/1986 | Kaiser ......................... 585/643 |
| 4,659,685 A | 4/1987 | Coleman, III et al. ...... 502/113 |
| 4,677,242 A | 6/1987 | Kaiser ......................... 585/638 |
| 4,677,243 A | 6/1987 | Kaiser ......................... 585/638 |
| 4,683,217 A | 7/1987 | Lok et al. .................... 502/214 |
| 4,684,617 A | 8/1987 | Lok et al. .................... 502/214 |
| 4,686,092 A | 8/1987 | Lok et al. .................... 423/306 |
| 4,686,093 A | 8/1987 | Flanigen et al. ............. 423/306 |
| 4,744,970 A | 5/1988 | Lok et al. .................... 423/306 |
| 4,752,651 A | 6/1988 | Kaiser ......................... 585/640 |
| 4,758,419 A | 7/1988 | Lok et al. .................... 423/306 |
| 4,814,541 A | 3/1989 | Lewis ......................... 585/640 |
| 4,861,938 A | 8/1989 | Lewis et al. ................. 585/640 |
| 4,861,968 A | 8/1989 | West ........................... 219/312 |
| 4,873,390 A | 10/1989 | Lewis et al. ................. 585/638 |
| 4,935,216 A | 6/1990 | Lok et al. .................... 423/328 |
| 4,943,424 A | 7/1990 | Miller ......................... 423/328 |
| 4,973,785 A | 11/1990 | Lok et al. .................... 585/481 |
| 4,973,792 A | 11/1990 | Lewis et al. ................. 585/638 |
| 5,087,347 A | 2/1992 | Miller .......................... 208/46 |
| 5,095,163 A | 3/1992 | Barger ......................... 585/640 |
| 5,126,308 A | 6/1992 | Barger et al. ................ 502/214 |
| 5,141,728 A | 8/1992 | Chang et al. ................ 423/328 |
| 5,147,626 A | 9/1992 | Chang et al. ................ 423/328 |
| 5,157,181 A | 10/1992 | Stine et al. .................. 585/329 |
| 5,174,976 A | 12/1992 | Chu et al. .................... 423/328 |
| 5,191,141 A | 3/1993 | Barger et al. ................ 585/640 |
| 5,227,151 A | 7/1993 | Calabro ....................... 423/703 |
| 5,233,117 A | 8/1993 | Barger ......................... 585/640 |
| 5,254,783 A | 10/1993 | Saleh et al. .................. 585/512 |
| 5,278,345 A | 1/1994 | Janssen et al. ............... 585/640 |
| 5,279,810 A | 1/1994 | Calabro ....................... 423/701 |
| 5,324,493 A | 6/1994 | Mueller et al. .............. 423/311 |
| 5,475,182 A | 12/1995 | Janssen ....................... 585/640 |
| 5,663,471 A | 9/1997 | Kvisle et al. ................ 585/639 |
| 5,714,662 A | 2/1998 | Vora et al. ................... 585/640 |

(List continued on next page.)

FOREIGN PATENT DOCUMENTS

| | | | |
|---|---|---|---|
| EP | 0642485 | 3/1995 | |
| EP | 1 127 862 | 8/2001 | ............. C07C/2/18 |
| GB | 1343949 | 1/1974 | ........... C07C/11/02 |
| WO | WO 93/24431 | 9/1993 | ........... C07C/11/02 |
| WO | WO97/36845 | 10/1997 | |
| WO | WO98/15496 | 4/1998 | |
| WO | WO 98/29363 | 9/1998 | ............. C07C/1/20 |
| WO | WO99/15482 | 4/1999 | |

OTHER PUBLICATIONS

Barger et al., "Converting Natural Gas to Ethylene and Propylene by the UOP/Hydro MTO Process," $12^{12}$ International Zeolite Conference 1999 Materials Research Society p. 567–573.

Blackwell et al., "Solid–State NMR of Silicoaluminosphate Molecular Sieves and Aluminophosphate Materials," J. Phys. Chem., 92, 3965–3970 (1988).

(List continued on next page.)

Primary Examiner—Walter D. Griffin

(57) ABSTRACT

Disclosed is a catalytic method for operating an oxygenate to olefins conversion reaction to provide a substantial quantity of prime olefin in the product. The product is provided by operating within desired parameters of weight hourly space velocity and oxygenate partial pressure. Operating the reaction to supply oxygenate at an oxygenate proportion index of at least 0.5, and controlling weight hourly space velocity and molar flow rate of oxygenate to the reactor to maintain a partial pressure-velocity compensation factor of at least 0.1 $psia^{-1}hr^{-1}$, a prime olefin selectivity of at least 45 wt. % can be maintained.

12 Claims, No Drawings

U.S. PATENT DOCUMENTS

| | | | | |
|---|---|---|---|---|
| 5,714,663 | A | 2/1998 | Serrand et al. | 585/648 |
| 5,744,680 | A | 4/1998 | Mulvaney, III et al. | 585/640 |
| 5,811,621 | A | 9/1998 | Van Dijk | 585/639 |
| 5,817,906 | A | 10/1998 | Marker et al. | 585/640 |
| 5,821,621 | A | 10/1998 | Jeng | 257/759 |
| 5,879,655 | A | 3/1999 | Miller et al. | 423/702 |
| 5,892,079 | A | 4/1999 | Wilson, Jr. | 556/11 |
| 5,904,880 | A | 5/1999 | Sun | 252/373 |
| 5,907,076 | A | 5/1999 | Ou et al. | 585/800 |
| 5,912,393 | A | 6/1999 | Barger et al. | 585/640 |
| 5,914,433 | A | 6/1999 | Marker | 585/313 |
| 5,925,586 | A | 7/1999 | Sun | 502/62 |
| 5,925,800 | A | 7/1999 | Sun et al. | 585/640 |
| 5,927,063 | A | 7/1999 | Janda et al. | 60/39.02 |
| 5,932,512 | A | 8/1999 | Sun | 502/214 |
| 5,952,538 | A | 9/1999 | Vaughn et al. | 585/640 |
| 5,960,643 | A | 10/1999 | Kuechler et al. | 62/620 |
| 5,962,762 | A | 10/1999 | Sun et al. | 585/640 |
| 5,972,203 | A | 10/1999 | Smith et al. | 208/113 |
| 5,990,367 | A | 11/1999 | Stine et al. | 585/514 |
| 5,990,369 | A | 11/1999 | Barger et al. | 585/640 |
| 6,004,898 | A | 12/1999 | Sun | 502/214 |
| 6,005,150 | A | 12/1999 | Vora | 585/639 |
| 6,005,155 | A | 12/1999 | Sun | 585/640 |
| 6,023,005 | A | 2/2000 | Lattner et al. | 585/639 |
| 6,040,257 | A | 3/2000 | Drake et al. | 502/64 |
| 6,040,264 | A | 3/2000 | Sun et al. | 502/214 |
| 6,046,371 | A | 4/2000 | Wu et al. | 585/638 |
| 6,046,373 | A | 4/2000 | Sun | 585/640 |
| 6,049,017 | A | 4/2000 | Vora et al. | 585/324 |
| 6,051,745 | A | 4/2000 | Wu et al. | 585/638 |
| 6,051,746 | A | 4/2000 | Sun et al. | 585/639 |
| 6,057,261 | A | 5/2000 | Sun | 502/341 |
| 6,137,022 | A | 10/2000 | Kuechler et al. | 585/638 |
| 6,531,639 | B1 * | 3/2003 | Fung et al. | 585/638 |

OTHER PUBLICATIONS

Bos et al., "Conversion of Methanol to Lower Olefins. Kinetic Modeling, Reactor Simulation, and Selection," Ind. Eng. Chem. Res. 1995, 34, 3808–3816.

Chang, "Methanol Conversion to Light Olefins," Catal. Rev.–Sci. Eng., 26(3&4), 323–345 (1984).

De Chen et al., "Dimethyl ether conversion to light olefins over SAPO–34; Deactivation due to coke deposition," Natural Gas Conversion V Studies in Surface Science and Catalysis, vol. 119 p. 521–526 (1998).

Eng et al, "Integration of the UOP/Hydro MTO Process into Ethylene Plants," 10$^{th}$ Ethylene Producers' Conference (1998).

Grace, Avidan & Knowlton, eds., "Experimental Techniques," Circulating Fluidized Beds, Blackie, 1997 (336–337).

Grace, J.R. and Bi, H. In Circulating Fluidized Beds; Grace, J. R., Avidan, A. A., Knowlton, T.M., Eds.; Blackie Academic & Professional; London, 1997, p 4.

Kaeding et al., "Production of Chemicals from Methanol," Journal of Catalysis 61, 155–164 (1980).

Lewis et al., "Methanol to Olefins Process Using Silicoaluminophosphate Catalysts," Union Carbide Corporation, Dewitt & Company Incorporated, 1988 Petrochemical Review, Mar. 23–25, 1988.

Liang et al., "Characteristics and Performance of SAPO–34 Catalyst for Methanol–to–Olefin Conversion," Applied Catalysis, 64 (1990) 31–40.

Marchi et al., "Catalytic Conversion of Methanol to Light Alkenes on SAPO Molecular Sieves," Applied Catalysis, 71 (1991) 139–152.

Prakash et al., "Synthesis of SAPO–34: High Silicon Incorporation in the Presence of Morpholine as Template," J. Chem. Soc., Faraday Trans., 1994, 90(15), 2291–2296.

Vora et al., "Conversion of Natural Gas to Ethylene and Propylene: The Most–Profitable Option," Natural Gas Conversion V Studies in Surface Science and Catalysis, vol. 119 p. 955 (1998).

* cited by examiner

CATALYTIC PRODUCTION OF OLEFINS AT HIGH METHANOL PARTIAL PRESSURES

This application is a continuation of U.S. application Ser. No. 09/506,843, filed Feb. 18, 2000, now U.S. Pat. No. 6,531,639.

FIELD OF THE INVENTION

This invention relates to a method for converting oxygenates to olefins. More particularly, this invention relates to controlling the reaction process to maintain a partial pressure-velocity compensation factor of at least 0.1 psia$^-$ $_1$hr$^{-1}$ such that a prime olefin selectivity of at least 45 wt. % can be maintained.

BACKGROUND OF THE INVENTION

Olefins, particularly prime olefins (i.e., ethylene and propylene), have been traditionally produced from petroleum feedstocks by either catalytic or steam cracking. Oxygenates, however, are becoming desirable feedstocks for making prime olefins. Particularly desirable oxygenate feedstocks are alcohols, such as methanol and ethanol, dimethyl ether, methyl ethyl ether, diethyl ether, dimethyl carbonate, and methyl formate. Many of these oxygenates can be produced from a variety of sources including synthesis gas derived from natural gas; petroleum liquids; carbonaceous materials, including coal; recycled plastics; municipal wastes; or any appropriate organic material. Because of the wide variety of sources, alcohol, alcohol derivatives, and other oxygenates have promise as an economical, non-petroleum source for light olefin production.

One way of producing olefins is by the catalytic conversion of methanol using a silicoaluminophosphate (SAPO) molecular sieve catalyst. For example, U.S. Pat. No. 4,499, 327 to Kaiser, discloses making olefins from methanol using any of a variety of SAPO molecular sieve catalysts. The process can be carried out at a temperature between 300° C. and 500° C., a pressure between 0.1 atmosphere to 100 atmospheres, and a weight hourly space velocity (WHSV) of between 0.1 and 40 hr$^{-1}$.

It is generally desirable to make prime olefins in a reactor which operates at a high partial pressure of feedstock, since a greater mass of feed stock can be moved through a given reactor size/volume at a given time relative to a reactor operating at a lower partial pressure of feedstock. Alternatively, for a given mass of feedstock to be processed through a reactor, the reactor size at a higher partial pressure of feedstock will be smaller and less expensive relative to a reactor operating at a lower partial pressure of feed stock.

It is also desirable to operate a reactor at a higher weight hourly space velocity (WHSV). Operating at higher WHSVs will enable the reactor volume and catalyst volume to be reduced for a given level of production.

Further, it is generally desirable to operate a reactor using a relatively low proportion of diluent. As the diluent level increases, reactor volume will necessarily increase, without a corresponding increase in feed stock throughput capability. The use of significant quantities of diluent also increases the complexity of the overall process of producing olefins in that the diluent must be separated and recovered, which requires additional facilities in the production process.

Reaching a more desirable level of higher feedstock partial pressure and WHSV, at a relatively low diluent concentration is, therefore, particularly desirable in order to increase the commercial desirability of oxygenates as alternative feedstocks. Unfortunately, in the oxygenate reaction process, increasing the partial pressure of oxygenate to a reactor will oftentimes have deleterious effects on the selectivities of the reaction to desired products, particularly prime olefins, to the point where operation beyond a certain partial pressure is undesirable. Reductions in diluent content of the feedstock may also increase the partial pressure of oxygenate to a reactor, thereby resulting in a decrease of selectivity to prime olefins. Similarly, increasing the WHSV may result in decreased oxygenate conversion. Therefore, operating parameters are needed in order to maintain acceptable levels of prime olefin selectivity in oxygenate conversion processes. Otherwise, the alternative use of oxygenate feedstocks to produce prime olefins will not exceed desirability over conventional petroleum processes.

SUMMARY OF THE INVENTION

In order to maintain desirable levels of prime olefin selectivity in catalytically converting oxygenate to olefin product at commercial scale, this invention provides, in one embodiment, a method for making olefin product from an oxygenate-containing feedstock. The method comprises providing a non-zeolite catalyst; and contacting the catalyst in a reactor with an oxygenate-containing feedstock at an oxygenate partial pressure of greater than 20 psia, preferably at least 25 psia, more preferably at least 30 psia.

It is desirable that the catalyst be contacted with the feedstock at a weight hourly space velocity of greater than 2 hr$^{-1}$, preferably in a range of from 5 hr$^{-1}$ to 1000 hr$^{-1}$, more preferably in a range of from 5 hr$^{-1}$ to 500 hr$^{-1}$. It is also desirable that the oxygenate be supplied to the reactor at an oxygenate proportion index of at least 0.5, preferably at least 0.6, more preferably at least 0.7.

The oxygenate-containing feedstock preferably comprises at least one compound selected from the group consisting of methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof It is particularly desirable that the oxygenate be methanol or dimethyl ether.

The non-zeolite catalyst used in the process preferably comprises a silicoaluminophosphate molecular sieve and a binder. Desirably silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, and mixtures thereof It is particularly desirable that the silicoaluminophosphate molecular sieve be SAPO-34 or SAPO-18, most particularly SAPO-34.

The oxygenate-containing feedstock can be contacted at a wide range of temperatures. Preferably, the oxygenate-containing feedstock is contacted with the silicoaluminophosphate catalyst at 200° C. to 700° C.

In an alternative embodiment, the average gas superficial velocity is maintained above a minimum level. Desirably, the oxygenate-containing feedstock is contacted with the silicoaluminophosphate catalyst in a reactor at an average gas superficial velocity of greater than 1 meter per second.

In yet another alternative embodiment, this invention provides a method for operating an oxygenate to olefins reaction. The method comprises providing a non-zeolite catalyst; providing an oxygenate-containing feedstock at an oxygen proportion index of at least 0.5; contacting the catalyst and the oxygenate-containing feedstock in a reactor and providing product from the reactor having a prime olefin selectivity of at least 45 wt. %; and maintaining a partial pressure-velocity compensation factor at a level of at least 0.1 psia$^{-1}$hr$^{-1}$ by controlling weight hourly space velocity and molar flow rate of oxygenate to the reactor.

In a preferred embodiment, the weight hourly space velocity and molar flow rate of oxygenate to the reactor are controlled to maintain a partial pressure-velocity compensation factor of at least 0.15 psia$^{-1}$hr$^{-1}$, more preferably at least 0.2 psia$^{-1}$hr$^{-1}$.

In controlling the oxygenate to olefins reaction process it is particularly desirable to operate at a relatively high oxygenate proportion index. Particularly desirable is to operate at an oxygenate proportion index of at least 0.6. Even more desirable is to operate at an oxygenate proportion index of at least 0.7.

The oxygenate to olefins reaction process can be controlled over a wide range of weight hourly space velocities. It is, however, particularly desirable to operate at a weight hourly space velocity of at least 2 hr$^{-1}$. Preferably, the process is operated at a weight hourly space velocity in the range of from 2 hr$^{-1}$ to 1000 hr$^{-1}$, more preferably at a range of from 5 hr$^{-1}$ to 500 hr$^{-1}$.

The invention also includes products made according to the methods provided. The products include the olefin product made directly from the oxygenate reaction process, as well as the derivative products of the prime olefins produced. Polyolefins are particularly desirable products which can be produced from the prime olefins of this invention.

In a particularly desirably embodiment, the catalyst and the oxygenate-containing feedstock are contacted in the reactor and the product from the reactor is provided at a prime olefin selectivity of at least 62 wt. %; and the partial pressure-velocity compensation factor is maintained at a level of at least 0.1 psia$^{-1}$hr$^{-1}$ by controlling weight hourly space velocity and molar flow rate of oxygenate to the reactor. Preferably, the product from the reactor is provided at a prime olefin selectivity of at least 70 wt. %; and the partial pressure-velocity compensation factor is maintained at a level of at least 0.15 psia$^{-1}$hr$^{-1}$ by controlling weight hourly space velocity and molar flow rate of oxygenate to the reactor.

DETAILED DESCRIPTION OF THE INVENTION

This invention provides a method for operating an oxygenate to olefins conversion reaction to provide a substantial quantity (i.e., high selectivity) of desirable prime olefin compounds in the product. As used herein, prime olefins refer to the combination of ethylene and propylene in the product. Thus, prime olefin selectivity is defined as the sum of the weight percent selectivity of ethylene and propylene in the product stream. Selectivity is defined in terms of the products of the reaction only, and unreacted feedstock and diluents are not considered. The weight percent selectivity of a given species in a reaction product is determined by taking the weight percent of that species in a reaction product and dividing it by the sum of the weight percents of all non-feedstock and non-diluent species in the reaction product.

The oxygenate to olefin conversion reaction is accomplished using a non-zeolite molecular sieve catalyst, with the feed comprising a relatively high concentration of oxygenate. The high selectivity to prime olefin using a relatively a high concentration of oxygenate in the feed is provided by controlling given parameters within a desired range.

In one embodiment, prime olefin selectivity of at least 45 wt. % can be achieved by controlling molar flow rate of oxygenate fed to the reactor and weight hourly space velocity (WHSV). As defined herein, weight hourly space velocity is defined as:

(weight of oxygenate fed to the reactor per hour+weight of reactive hydrocarbon fed to the reactor per hour)
weight of molecular sieve within the reactor The molar flow rate of oxygenate fed to the reactor and the weight hourly space velocity are to be controlled above a minimum oxygen proportion index and a minimum partial pressure-velocity compensation factor.

The oxygenate proportion index is defined herein as:

$$\frac{\text{moles of oxygenate fed to the reactor per hour}}{(\text{moles of oxygenate fed to the reactor per hour} + \text{moles of diluent fed to the reactor per hour})}$$

Preferably, the molar flow rate of oxygenate fed to the reactor and the weight hourly space velocity is controlled such that the oxygenate proportion index is maintained at a level of at least 0.5, more preferably at least 0.6, most preferably at least 0.7.

The partial pressure-velocity compensation factor is defined herein as WHSV divided by the partial pressure of the oxygenate at the reactor inlet. For the purposes of this invention, the partial pressure of the oxygenate to the reactor can be calculated as the total moles of oxygenate feed to the reactor per hour times the total reactor pressure, that product divided by the total number of moles of all species to the reactor per hour. In the event a total pressure gradient exists in the reactor, the total reactor pressure is determined as the lowest pressure in the reactor, usually at a reactor outlet. In the event of multiple reactor inlet locations, the moles of oxygenate feed to the reactor is determined as the sum of the moles of oxygenates to all inlets to the reactor per hour, and the total moles of all species is determined as the sum of all the moles of species to all inlets to the reactor per hour. Preferably, the partial pressure of oxygenate to the reactor is at least 20 psia, more preferably at least 25 psia, and most desirably at least 30 psia.

The partial pressure-velocity compensation factor is defined herein as WHSV divided by the partial pressure of the oxygenate to the reactor. Preferably, the molar flow rate of oxygenate fed to the reactor and the weight hourly space velocity are controlled such that the partial pressure-velocity compensation factor is maintained at least 0.1 psia$^{-1}$hr$^{-1}$, preferably at least 0.15 psia$^{-1}$hr$^{-1}$, more preferably at least 0.2 psia$^{-1}$hr$^{-1}$, and most desirably at least 0.5 psia$^{-1}$hr$^{-1}$. In certain desirable embodiments, the reactor will be operated at a partial pressure-velocity compensation factor of between 0.1 and 100 psia$^{-1}$hr$^{-1}$, more preferably between 0.15 and 50 psia$^{-1}$hr$^{-1}$, and most desirably between 0.2 and 25 psia$^{-1}$hr$^{-1}$ A desired level of prime olefin selectivity can be maintained by maintaining the partial pressure-velocity compensation factor above a minimum level. For example, a prime olefin selectivity of at least about 62 wt. % can be maintained by maintaining the partial pressure-velocity compensation factor at a level of at least 0.1 psia$^{-1}$hr$^{-1}$, more preferably at least about 0.15 psia$^{-1}$hr$^{-1}$. Further, a prime olefin selectivity of at least about 70 wt. % can be maintained by maintaining the partial pressure-velocity compensation factor at a level of at least 0.15 psia$^{-1}$hr$^{-1}$, more preferably at least about 0.2 psia$^{-1}$hr$^{-1}$.

The catalyst that is used in this invention is one that incorporates a non-zeolite molecular sieve. This type of molecular sieve comprises a three-dimensional microporous crystal framework structure of $[AlO_2]$ and $[PO_2]$ tetrahedral units. Non-zeolite molecular sieves are conventionally made by preparing an aqueous mixture of a phosphorus containing compound and an aluminum containing compound at an $Al_2O_3:P_2O_5$ molar ratio of greater than about 0.3, and maintaining the mixture at conditions suitable for crystals of the molecular sieve to form. Examples of such molecular sieves include those disclosed in U.S. Pat. Nos. 4,310,440; 4,440,871; 4,500,651; 4,554,143; 4,567,029; 4,683,217; 4,684,617; 4,686,093; 4,744,970; 4,758,419; 4,935,216; 4,943,424; 4,973,785, and 5,879,655, the descriptions of which are incorporated herein by reference.

Particularly preferred non-zeolite molecular sieves include silicoaluminophosphate (SAPO) molecular sieves. The SAPO molecular sieves also include a $[SiO_2]$ tetrahedral unit in the microporous crystal framework structure. The way Si is incorporated into the structure can be determined by $^{29}Si$ MAS NMR. See Blackwell and Patton, *J. Phys. Chem.*, 92, 3965 (1988). The desired SAPO molecular sieves will exhibit one or more peaks in the $^{29}Si$ MAS NMR, with a chemical shift $\Lambda(Si)$ in the range of −88 to −96 ppm and with a combined peak area in that range of at least 20% of the total peak area of all peaks with a chemical shift $\Lambda(Si)$ in the range of −88 ppm to −115 ppm, where the $\Lambda(Si)$ chemical shifts refer to external tetramethylsilane (TMS).

It is preferred that the silicoaluminophosphate molecular sieve used in this invention have a relatively low $Si/Al_2$ ratio. In general, the lower the $Si/Al_2$ ratio, the lower the $C_1$–$C_4$ saturates selectivity, particularly propane selectivity. A $Si/Al_2$ ratio of less than 0.65 is desirable, with a $Si/Al_2$ ratio of not greater than 0.40 being preferred, and a $Si/Al_2$ ratio of not greater than 0.32 being particularly preferred. A $Si/Al_2$ ratio of not greater than 0.20 is most preferred.

Silicoaluminophosphate molecular sieves are generally classified as being microporous materials having 8, 10, or 12 membered ring structures. These ring structures can have an average pore size ranging from about 3.5–15 angstroms. Preferred are the small pore SAPO molecular sieves having an average pore size ranging from about 3.5 to 5 angstroms, more preferably from 4.0 to 5.0 angstroms. These pore sizes are typical of molecular sieves having 8 membered rings.

In general, silicoaluminophosphate molecular sieves comprise a molecular framework of corner-sharing $[AlO_2]$, $[PO_2]$, and $[SiO_2]$ tetrahedral units. This type of framework is effective in converting various oxygenates into olefin products.

The $[AlO_2]$ tetrahedral units within the framework structure of the non-zeolite molecular sieve can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive phosphorus-containing compositions under the appropriate conditions to form the molecular sieve.

The $[PO_2]$ tetrahedral units within the framework structure of the non-zeolite molecular sieve can be provided by a variety of compositions. Examples of these phosphorus-containing compositions include phosphoric acid, organic phosphates such as triethyl phosphate, and aluminophosphates. The phosphorous-containing compositions are mixed with reactive aluminum-containing compositions under the appropriate conditions to form the molecular sieve.

In the preferred SAPO non-zeolite molecular sieve, the $[SiO_2]$ tetrahedral units within the framework structure can be provided by a variety of compositions. Examples of these silicon-containing compositions include silica sols and silicium alkoxides such as tetra ethyl orthosilicate. The silicon-containing compositions are mixed with reactive aluminum and phosphorus-containing compositions under the appropriate conditions to form the molecular sieve.

Substituted SAPOs can also be used in this invention. These compounds are generally known as MeAPSOs or metal-containing silicoaluminophosphates. The metal can be alkali metal ions (Group IA), alkaline earth metal ions (Group IIA), rare earth ions (Group IIIB, including the lanthanoid elements: lanthanum, cerium, praseodymium, neodymium, samarium, europium, gadolinium, terbium, dysprosium, holmium, erbium, thulium, ytterbium and lutetium; and scandium or yttrium) and the additional transition cations of Groups IVB, VB, VIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a $[MeO_2]$ tetrahedral unit. The $[MeO_2]$ tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished adding the metal component during synthesis of the molecular sieve. However, post-synthesis ion exchange can also be used.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, mixtures thereof, and intergrowths thereof. Preferred are SAPO-18, SAPO-34, SAPO-35, SAPO-44, and SAPO-47, particularly SAPO-18 and SAPO-34, including the metal containing forms thereof, mixtures thereof, and intergrowths thereof. As used herein, the term mixture is synonymous with combination and is considered a composition of matter having two or more components in varying proportions, regardless of their physical state. The term intergrowth, or intergrowths, means that the molecular sieve is not a simple mixture of crystalline structures, but that the molecular seive can have a crystalline structure having more than one type of framework. For example, a crystalline structure could have SAPO-34 as a main structure, yet have SAPO-18 as an intergrowth or contained as part of the overall crystalline structure.

An aluminophosphate (ALPO) molecular sieve is another preferred embodiment of a non-zeolite molecular sieve which can be used in this invention. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPO structures are ALPO-5, ALPO-11, ALPO-18, ALPO-31, ALPO-34, ALPO-36, ALPO-37, and ALPO-46.

The ALPOs can also include a metal substituent in the framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica-aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AlO_2$ and $PO_2$ tetrahedral units. These as manufactured structures (which contain template prior to calcination) can be represented by empirical chemical composition, on an anhydrous basis, as:

$$mR: (M_xAl_yP_z)O_2$$

wherein "R" represents at least one organic templating agent present in the intracrystalline pore system; "m" represents the moles of "R" present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, "x", "y", and "z" represent the mole fractions of the metal "M", (i.e. magnesium, manganese, zinc and cobalt), aluminum and phosphorus, respectively, present as tetrahedral oxides.

The metal containing ALPOs are sometimes referred to by the acronym as MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The non-zeolite molecular sieves are synthesized by conventional hydrothermal crystallization methods. A reaction mixture is formed by mixing together reactive aluminum and phosphorus components, and optionally reactive silicon or other reactive metal components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring or seeding with crystalline material will facilitate the formation of the product.

Typically, the molecular sieve product will be formed in solution. It can be recovered by standard means, such as by centrifugation or filtration. The product can also be washed, recovered by the same means and dried.

As a result of the crystallization process, the recovered sieve contains within its pores at least a portion of the template used in making the initial reaction mixture. The crystalline structure essentially wraps around the template, and the template must be removed so that the molecular sieve can exhibit catalytic activity. Once the template is removed, the crystalline structure that remains has what is typically called an intracrystalline pore system.

In many cases, depending upon the nature of the final product formed, the template may be too large to be eluted from the intracrystalline pore system. In such a case, the template can be removed by a heat treatment process. For example, the template can be calcined, or essentially combusted, in the presence of an oxygen-containing gas, by contacting the template-containing sieve in the presence of the oxygen-containing gas and heating at temperatures from 200° C. to 900° C. In some cases, it may be desirable to heat in an environment having a low oxygen concentration. In these cases, however, the result will typically be a breakdown of the template into a smaller component, rather than by the combustion process. This type of process can be used for partial or complete removal of the template from the intracrystalline pore system. In other cases, with smaller templates, complete or partial removal from the sieve can be accomplished by conventional desorption processes such as those used in making standard zeolites.

The reaction mixture can contain one or more templates. Templates are structure directing or structure affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly directing than another.

Representative templates include tetraethyl ammonium salts, cyclopentylamine, aminomethyl cyclohexane, piperidine, triethylamine, cyclohexylamine, tri-ethyl hydroxyethylamine, morpholine, dipropylamine (DPA), pyridine, isopropylamine and combinations thereof. Preferred templates are triethylamine, cyclohexylamine, piperidine, pyridine, isopropylamine, tetraethyl ammonium salts, dipropylamine, and mixtures thereof The tetraethylammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate.

The SAPO molecular sieve structure can be effectively controlled using combinations of templates. For example, in a particularly preferred embodiment, the SAPO molecular sieve is manufactured using a template combination of TEAOH and dipropylamine. This combination results in a particularly desirable SAPO structure for the conversion of oxygenates, particularly methanol and dimethyl ether, to light olefins such as ethylene and propylene.

The silicoaluminophosphate molecular sieve is typically admixed (blended) with other materials. When blended, the resulting composition is typically referred to as a SAPO catalyst, with the catalyst comprising the SAPO molecular sieve.

Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof These components are also effective in reducing, inter alia, overall catalyst cost, acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g–° C., more preferably from about 0.1 to about 0.8 cal/g–° C., most preferably from about 0.1 to about 0.5 cal/g–° C.

Additional olefin-forming molecular sieve materials can be included as a part of the SAPO catalyst composition or as separate molecular sieve catalysts in admixture with the SAPO catalyst if desired. Structural types of small pore molecular sieves that are suitable for use in this invention include AEI, AFT, APC, ATN, ATT, ATV, AWW, BIK, CAS, CHA, CIU, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include MFI, MEL, MTW, EUO, MTT, HEU, FER, AFO, AEL, TON, and substituted forms thereof These small and medium pore molecular sieves are described in greater detail in the *Atlas of Zeolite Structural Types*, W. M. Meier and D. H. Olsen, Butterworth Heineman, 3rd ed., 1997, the detailed description of which is explicitly incorporated herein by reference. Preferred molecular sieves which can be combined with a silicoaluminophosphate catalyst include ZSM-5, ZSM-34, erionite, and chabazite.

The catalyst composition preferably comprises about 1% to about 99%, more preferably about 5% to about 90%, and most preferably about 10% to about 80%, by weight of molecular sieve. It is also preferred that the catalyst composition have a particle size of from about 20 T to 3,000 T, more preferably about 30 T to 200 T, most preferably about 50 T to 150 T.

The catalyst can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof Another embodiment of this invention includes a method for making olefin product from an oxygenate feed stock. At the appropriate match of oxygenate partial pressure, weight hourly space velocity, and oxygenate proportion index, a substantially high prime olefin selectivity can be achieved.

In the methods of this invention, a feed containing an oxygenate, and optionally a diluent or a hydrocarbon added separately or mixed with the oxygenate, is contacted with a catalyst containing a SAPO molecular sieve in a reaction zone or volume. The volume in which such contact takes place is herein termed the "reactor," which may be a part of a "reactor apparatus" or "reaction system." Typically there is one inlet of feedstock to the reaction zone, and one outlet of reaction product. However, there may be instances where multiple inlets of feedstock to the reaction zone or multiple outlets of reaction product from the reaction zone are utilized, and such instances are covered by the present invention. In such instances, invention parameters utilizing feedstock are based on the total of all feedstock to all inlets to the reaction zone, and invention parameters on the reaction product are based on any one of the outlets of the reaction zone. Another part of the reaction system may be a "regenerator," which comprises a volume wherein carbonaceous deposits (or coke) on the catalyst resulting from the olefin conversion reaction are removed by contacting the catalyst with regeneration medium.

The oxygenate feedstock of this invention comprises at least one organic compound which contains at least one oxygen atom, such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; $C_4$–$C_{20}$ alcohols; methyl ethyl ether; dimethyl ether; diethyl ether; di-isopropyl ether; formaldehyde; dimethyl carbonate; dimethyl ketone; acetic acid; and mixtures thereof Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidation.

One or more inert diluents may be present in the feedstock in order to maintain an oxygenate proportion index of at least 0.5. As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof The preferred diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of reactor product.

In the process of this invention, coked catalyst can be regenerated by contacting the coked catalyst with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

Catalyst that has been contacted with feed in a reactor is defined herein as "feedstock exposed." Feedstock exposed catalyst will provide olefin conversion reaction products having substantially lower propane and coke content than a catalyst which is fresh and regenerated. A catalyst will typically provide lower amounts of propane as it is exposed to more feed, either through increasing time at a given feed rate or increasing feed rate over a given time.

At any given instant in time, some of the catalyst in the reactor will be fresh, some regenerated, and some coked or partially coked as a result of having not yet been regenerated. Therefore, various portions of the catalyst in the reactor will have been feedstock exposed for different periods of time. Since the rate at which feed flows to the reactor can vary, the amount of feed to which various portions of the catalyst can also vary. To account for this variation, the Average Catalyst Feedstock Exposure (ACFE) index is used to quantitatively define the extent to which the entire catalyst in the reactor has been feedstock exposed.

As used herein, ACFE index is the total weight of feed divided by the total weight of molecular sieve (i.e., excluding binder, inerts, etc., of the catalyst composition) sent to the reactor, including both fresh and regenerated catalyst. The measurement should be made over an equivalent time interval, and the time interval should be long enough to smooth out fluctuations in catalyst or feedstock rates according to the reactor and regeneration process step selected to allow the system to viewed as essentially continuous. In the case of reactor systems with periodic regenerations, this can range from hours up to days or longer. In the case of reactor systems with substantially constant regeneration, minutes or hours may be sufficient.

Flow rate of catalyst can be measured in a variety of ways. In the design of the equipment used to carry the catalyst between the reactor and regenerator, the catalyst flow rate can be determined given the coke production rate in the reactor, the average coke level on catalyst leaving the reactor, and the average coke level on catalyst leaving the regenerator. In an operating unit with continuous catalyst flow, a variety of measurement techniques can be used. Many such techniques are described, for example, by Michel Louge, "Experimental Techniques," *Circulating Fluidized Beds*, Grace, Avidan, & Knowlton, eds., Blackie, 1997 (336–337), the descriptions of which are expressly incorporated herein by reference.

In this invention, only the molecular sieve in the catalyst sent to the reactor may be used in the determination of ACFE index. The catalyst sent to the reactor, however, can be either fresh or regenerated or a combination of both. Molecular sieve which may be recirculated to and from the reactor within the reactor apparatus (i.e., via ducts, pipes or annular regions), and which has not been regenerated or does not contain fresh catalyst, is not to be used in the determination of ACFE index.

In a preferred embodiment of this invention, a feed containing an oxygenate, and optionally a hydrocarbon, either separately or mixed with the oxygenate, is contacted with a catalyst containing a SAPO molecular sieve at process conditions effective to produce olefins in a reactor where the catalyst has an ACFE index of at least about 1.0, preferably at least 1.5. An ACFE index in the range of about 1.0 to 20 is effective, with a range of about 1.5–15 being desirable. A range of about 2–12 is particularly preferred.

The process is effectively carried out at an oxygenate partial pressure of greater than 20 psia. Preferably, the oxygenate partial pressure is at least about 25 psia, more preferably at least about 30 psia. For practical design purposes it is desirable to operate at a methanol partial pressure of not greater than about 500 psia, preferably not greater than about 400 psia, most preferably not greater than about 300 psia.

Any standard reactor system can be used, including fixed bed, fluid bed or moving bed systems. Preferred reactors are co-current riser reactors and short contact time, countercurrent free-fall reactors in which an oxygenate feedstock can be contacted with a molecular sieve catalyst at a WHSV of at least about 2 $hr^{-1}$, preferably in the range of from about 2 $hr^{-1}$ to 1000 $hr^{-1}$, and most preferably in the range of from about 5 $hr^{-1}$ to 500 $hr^{-1}$. WHSV is defined herein as the weight of oxygenate, and any hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and hydrocarbon which may be present, and the molecular sieve contained in the catalyst.

The process can also be operated according to a desired gas superficial velocity (GSV). Preferably, an average gas superficial velocity of greater than about 1 meter per second (m/s) is maintained in the reactor. Preferably, the average gas superficial velocity is greater than about 2 m/s. More preferably, the average gas superficial velocity is between a range of 2–6 m/s.

As defined herein, gas superficial velocity is the volumetric flow rate of the feedstock (including oxygenate, hydrocarbon, and any diluent) divided by the reactor cross-sectional area. Since feedstock is converted to olefin product while flowing through the reactor, the volumetric flow rate of the feedstock varies throughout the reactor. In addition, depending upon reactor design, the cross-sectional area of the reactor may also vary at any given point within the reactor. Therefore, average gas superficial velocity as used herein represents the average gas superficial velocity throughout the reactor.

When the average gas superficial velocity is greater than about 1 m/s, back-mixing of gases in the reactor is minimized. This increases the selectivity to the desired light olefins, i.e., ethylene and/or propylene, and increases the approach to plug flow behavior of the gases flowing through the reactor. The velocity profile at a given cross section of the reactor is approximately flat and there is little axial diffusion or back-mixing of fluid elements. Ideal plug flow behavior occurs when elements of the homogeneous fluid reactant move through a reactor as plugs moving parallel to the reactor axis.

This invention also enables an increase in reactor capacity, while maintaining a stable POS. As defined herein, a stable POS is one that is within about 10 wt. %, preferably about 5 wt. % of that obtained using essentially 100% oxygenate as the feed at a pressure of 25 psig.

The invention also enables an increase in reactor capacity while maintaining a stable conversion of oxygenate across the reactor. As defined herein, stable oxygenate conversion is an oxygenate conversion that is one that is within about 15 wt. %, preferably about 10 wt. % of that obtained using essentially 100% oxygenate as the feed at a pressure of 25 psig. Such stable conversion can be maintained while maintaining a stable POS.

Preferably, the oxygenate feed is contacted with the catalyst when the oxygenate is in a vapor phase. The oxygenate feed can also be fed in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature range can be from about 200° C. to 700° C., preferably from about 300° C. to 600° C., more preferably from about 350° C. to 550° C. At the lower end of the temperature range, the formation of the desired olefin products may become markedly slow. At the upper end of the temperature range, the process may not form an optimum amount of product.

The conversion of oxygenates to produce light olefins may be carried out in a variety of catalytic reactors. Reactor types include fixed bed reactors, fluid bed reactors, and concurrent riser reactors as described in "Free Fall Reactor,"

*Fluidization Engineering*, D. Kunii and O. Levenspiel, Robert E. Krieger Publishing Co. NY, 1977, expressly incorporated herein by reference. Additionally, countercurrent free fall reactors may be used in the conversion process as described in U.S. Pat. No. 4,068,136 and "Riser Reactor", *Fluidization and Fluid–Particle Systems*, pages 48–59, F. A. Zenz and D. F. Othmo, Reinhold Publishing Corp., NY 1960, the detailed descriptions of which are also expressly incorporated herein by reference.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, NO, $NO_2$, $N_2O_5$, and mixtures thereof. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with feed. Typical regeneration temperatures are in the range of 250–700° C., desirably in the range of 350–700° C. Preferably, regeneration is carried out at a temperature range of 450–700° C.

It is desirable to strip at least some of the volatile organic components which may be adsorbed onto the catalyst or located within its microporous structure prior to entering the regenerator. This can be accomplished by passing a stripping gas over the catalyst in a stripper or stripping chamber, which can be located within the reactor or in a separate vessel. The stripping gas can be any substantially inert medium that is commonly used. Examples of stripping gas are steam, nitrogen, helium, argon, methane, $CO_2$, CO, flue gas, and hydrogen.

It may be desirable to cool at least a portion of the regenerated catalyst to a lower temperature before it is sent back to the reactor. A heat exchanger located externally to the regenerator may be used to remove some heat from the catalyst after it has been withdrawn from the regenerator. When the regenerated catalyst is cooled, it is desirable to cool it to a temperature which is from about 200° C. higher to about 200° C. lower than the temperature of the catalyst withdrawn from the reactor. More desirably, it is cooled to a temperature from about 10–200° C. lower than the temperature of the catalyst withdrawn from the reactor. This cooled catalyst then may be returned to either some portion of the reactor, the regenerator, or both. When the regenerated catalyst from the regenerator is returned to the reactor, it may be returned to the reactor's catalyst disengaging zone, the reaction zone, and/or the inlet zone. Introducing the cooled catalyst into the reactor or regenerator serves to reduce the average temperature in the reactor or regenerator.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor.

It is preferred the catalyst within the reactor have an average level of coke effective for selectivity to ethylene and/or propylene. Preferably, the average coke level on the catalyst will be from about 2 wt. % to about 30 wt. %, more preferably from about 2 wt. % to about 20 wt. %. In order to maintain this average level of coke on catalyst, the entire volume of catalyst can be partially regenerated under conditions effective to maintain the desired coke content on catalyst. It is preferred, however, to recycle only a portion of the coked catalyst for feed contact without regenerating. This recycle can be performed either internal or external to the reactor. The portion of coked catalyst to be regenerated is preferably regenerated under conditions effective to obtain a regenerated catalyst having a coke content of less than 2 wt. %, preferably less than 1.5 wt. %, and most preferably less than 1.0 wt. %.

In order to make up for any catalyst loss during the regeneration or reaction process, fresh catalyst can be added. Preferably, the fresh catalyst is added to the regenerated catalyst after it is removed from the regenerator, and then both are added to the reactor. However, the fresh catalyst can be added to the reactor independently of the regenerated catalyst. Any amount of fresh catalyst can be added, but it is preferred that an ACFE index of at least 1.5 be maintained.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

EXAMPLE 1

Experiments using a SAPO-34 catalyst (50% SAPO-34/50% binder) were carried out in a fluidized-batch-recirculating (FBR) reactor at a gas-recirculating rate of 10 circulations per second. The circulation rate was much higher than the reaction rate, and the reactor was considered as a non-gradient batch reactor. The catalyst particles were placed in a basket bound by two sintered-porous disks. An impeller rotating at 6000–7000 rpm circulated the gas in the reactor from the top of the basket through the annulus space to the bottom of the basket. The gas entered the bottom of the basket at a speed sufficient to fluidize the catalyst particles. Catalyst particles were in turbulent fluidization condition with very limited amount of gas bubbles in the suspension. Gas residence time was controlled by time-programmed valves that emptied the reactor gas to a large vacuum vessel. A gas chromatograph (GC) sampling valve was equipped in the gas depressure path to capture a gas sample for product composition analysis.

The reactor was initially charged with 0.3 grams of the catalyst and enough argon to achieve 60 psia reactor pressure. This was to ensure that the circulation of the argon gas by the fast rotation of the impeller can fluidize the catalyst particles before the injection of methanol so that there is good contact of methanol with the fluidized catalyst particles. The reaction time was controlled by venting the reactor gas at a preset time of 5 seconds. At the preset time, a vent valve was opened to vent the gas through a GC sampling valve to a vacuum vessel. The gas composition was determined by GC analysis. After the reaction products were removed from the reactor and the reactor was purged with argon, it was pressurized with argon to 60 psia and the impeller was operating to fluidize the catalyst particles before the next methanol injection was carried out.

The reaction was carried out under a constant reactor volume, 108 cc. Therefore, 0.3 cc of methanol injected into the reactor at 450° C. quickly vaporized to increase the reactor pressure by 60 psia. The concentration of methanol in this case was 60/(60+60)=50 mole %.

It was observed that catalyst activity increases significantly in the first few methanol injections (the activation process) and thereafter remains quite constant. The effect of pressure on catalyst performance was carried out after this activation process.

The activated catalyst remained in the reactor, and argon was introduced into the reactor to raise the reactor pressure to 60 psia. Variation of the methanol partial pressure was achieved by changing the injection volume of methanol injected into the reactor. Experiments were conducted from 0.3 to 0.5 cc in 0.1 cc increments, providing a partial pressure of oxygenate feed of 60, 80, and 100 psia, and an oxygenate concentration of 50, 57, and 62.5 mole %, respectively.

The space velocity (reactor capacity) was calculated according to the following formula.

$$\text{gMethanol/gSAPO-34/gas residence time} = [(0.3 \text{ cc} * 0.7914 \text{ g/cc}) /$$
$$0.3 \text{ g} * 50\% * 5 \text{ sec})]*$$
$$3600 \text{ sec/hr}$$
$$= (0.23742/0.15)*$$
$$(3600/5) \text{ g/g/hr}$$
$$= 380 \text{ hr}^{-1}$$

As the partial pressure of the oxygenate was increased from 60 psia to 80 and 100 psia, the space velocity was increased from 1140 to 1520, and 1900 hr$^{-1}$, respectively. The results are shown in Table 1.

TABLE 1

| Oxygenate Proportion Index | Oxygenate Partial Pressure (psia) | WHSV (hr$^{-1}$) | PPVCF (1/psia-hr) | Oxygenate Conversion (wt. %) | Ethylene Selectivity (wt. %) | Propylene Selectivity (wt. %) | POS (wt. %) |
|---|---|---|---|---|---|---|---|
| 0.5 | 60 | 1140 | 19 | 82 | 32 | 47 | 79 |
| 0.57 | 80 | 1520 | 19 | 73 | 31 | 44 | 75 |
| 0.625 | 100 | 1900 | 19 | 76 | 29 | 47 | 76 |

The data demonstrate the remarkable stability of reactor selectivity performance with corresponding increases in reactor capacity. By increases in reactor capacity is meant that more prime olefins are produced from the same reactor volume. Thus, someone operating an oxygenate conversion process comprising a fixed reactor volume may use the present invention to increase valuable output from the process without incurring substantial cost for increasing reactor volume (eg, adding an additional reactor, or lengthening an existing reactor, among other methods). In this example is demonstrated a particularly desirable embodiment of the invention with a stable conversion as well as a stable POS through widely varying oxygenate partial pressure and WHSV ranges.

EXAMPLE 2

A positive displacement pump was used to deliver liquid methanol at constant feed rate through a ⅛" capillary stainless steel line up to a 4-part Valco™ valve, which was connected to the bottom of a reactor. The methanol line was connected to port 1, a helium line was connected to port 2, port 3 was connected the reactor inlet, and port 4 was to vent.

The reactor, a ½"×½ ft stainless steel tube equipped with a 1.5" heating block, was positioned in a resistive furnace, and kept at constant temperature for isothermal operation. A glass wool plug was used to support the catalyst bed. A 5-point internal thermocouple was used to record and control temperature inside the catalyst bed.

The reactor effluent was flowed through a ⅛" capillary stainless steel line kept at 300° C. where it was mixed with 150 SCCM of helium. A backpressure regulator on the effluent line controlled reactor pressure. A slipstream of about 70 SCCM was flowed to a gas chromatograph (GC)

sampling system. The GC sampling system included two automated 16-port Valco™ valves in series. The valves were capable of sampling the effluent every 5 seconds. The samples were isolated in conventional sample loops. The GC sampling system was maintained at 300° C. Samples were subsequently injected into the GC and analyzed at the end of each run.

Methanol rate was typically 0.7 g/min and catalyst was adjusted to obtain the desired VHSV. Reactor temperature was first stabilized by flowing helium through the reactor and flowing methanol to the vent (i.e., port 4 of the reactor inlet valve). The runs were started when the reactor inlet valve was switched to allow methanol to flow into the reactor. This automatically activated the GC sampling system. The results are shown in Table 2.

TABLE 2

| Run | Oxygenate Proportion Index (OPI) | Oxygenate Partial Pressure (psia) | Oxygenate Conversion (wt. %) | WHSV (1/hr) | PPVCF (1/psia-hr) | C2= Selectivity | C3= Selectivity | POS (wt. %) |
|---|---|---|---|---|---|---|---|---|
| 1 | 1.0 | 94.7 | 99.4% | 2.00 | 0.02 | 26.3% | 21.7% | 48.0% |
| 2 | 1.0 | 95.7 | 99.3% | 5.00 | 0.05 | 32.1% | 29.9% | 61.9% |
| 3 | 1.0 | 91.2 | 99.7% | 10.00 | 0.11 | 32.2% | 33.2% | 65.4% |
| 4 | 1.0 | 94.7 | 87.2% | 25.0 | 0.26 | 34.9% | 41.4% | 76.3% |
| 5 | 1.0 | 95.7 | 64.7% | 50.0 | 0.52 | 31.8% | 42.5% | 74.2% |
| 6 | 1.0 | 39.7 | 99.0% | 2.5 | 0.06 | 32.6% | 28.3% | 60.9% |
| 7 | 1.0 | 39.7 | 99.5% | 5.0 | 0.13 | 35.2% | 32.9% | 68.1% |
| 8 | 1.0 | 39.7 | 99.5% | 10.0 | 0.25 | 37.6% | 35.5% | 73.0% |
| 9 | 1.0 | 39.7 | 42.4% | 50.0 | 1.26 | 33.4% | 41.5% | 74.9% |
| 10 | 1.0 | 39.7 | 37.6% | 79.9 | 2.01 | 32.2% | 42.2% | 74.4% |
| 11 | 1.0 | 39.7 | 41.8% | 80.1 | 2.02 | 34.2% | 42.5% | 76.7% |
| 12 | 1.0 | 39.7 | 15.4% | 95.0 | 2.39 | 31.7% | 42.8% | 74.5% |
| 13 | 1.0 | 39.7 | 5.4% | 150.1 | 3.78 | 30.7% | 41.9% | 72.6% |
| 14 | 0.58 | 12.0 | 98.9% | 2.0 | 0.17 | 36.2% | 32.3% | 68.5% |
| 15 | 0.58 | 12.0 | 98.6% | 5.0 | 0.42 | 41.4% | 35.5% | 76.9% |
| 16 | 0.58 | 12.0 | 92.5% | 10.1 | 0.84 | 40.9% | 35.0% | 75.9% |
| 17 | 0.58 | 12.0 | 45.9% | 25.0 | 2.08 | 40.2% | 38.9% | 79.1% |
| 18 | 0.58 | 12.0 | 33.1% | 50.0 | 4.17 | 38.6% | 38.3% | 76.9% |

The data in Table 2 demonstrate the improvement in POS occurring at PPVCF of about 0.1 and greater. In addition, they support the data provided in Table 1 indicating a stable POS when maintaining a PPVCF of 0.1 or greater. For example, note that in Run 7 and Run 14, with close PPVCF's of 0.13 and 0.17, respectively, the POS are stable at 68.1% and 68.5%, respectively. This is a remarkable, unexpected result considering oxygenate partial pressure and WHSV differences of a factor of over 2.5. Run 7 and Run 14 also demonstrate an instance of the present invention providing stable conversions of oxygenate feedstock, and again demonstrate the unique capability of the present invention to provide high POS with increasing reactor capacity, as discussed in Example 1.

Having now fully described this invention, it will be appreciated by those skilled in the art that the invention can be performed within a wide range of parameters within what is claimed, without departing from the spirit and scope of the invention.

What is claimed is:

1. A method for making a polyolefin product from an oxygenate-containing feedstock, comprising
   providing a non-zeolite catalyst; and
   contacting the catalyst in a reactor with an oxygenate-containing feedstock at an oxygenate partial pressure of greater than 20 psia, a weight hourly space velocity of greater than 2 hr$^{-1}$, an average gas superficial velocity of greater than 1 meter per second, and an oxygenate proportion index of at least 0.5, thereby forming an olefin product; and
   polymerizing the olefin product to form the polyolefin product.

2. The method of claim 1, wherein the oxygenate partial pressure is at least 25 psia.

3. The method of claim 1, wherein the oxygenate partial pressure is at least 30 psia.

4. The method of claim 1, wherein the weight hourly space velocity is in a range of from 2 hr$^{-1}$ to 1000 hr$^{-1}$.

5. The method of claim 1, wherein the weight hourly space velocity is in a range of from 5 hr$^{-1}$ to 500 hr$^{-1}$.

6. The method of claim 1, wherein the oxygenate proportion index is at least 0.6.

7. The method of claim 1, wherein the oxygenate proportion index is at least 0.7.

8. The method of claim 1, wherein the oxygenate-containing feedstock comprises at least one compound selected from the group consisting of methanol; ethanol; n-propanol; isopropanol; C4–C20 alcohols; methyl ethyl ether; dimethyl ether; diethyl ether; di-isopropyl ether; formaldehyde; dimethyl carbonate; dimethyl ketone; acetic acid; and mixtures thereof.

9. The method of claim 1, wherein the catalyst comprises a silicoaluminophosphate molecular sieve and a binder.

10. The method of claim 9, wherein the silicoaluminophosphate molecular sieve is selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, metal containing forms thereof, mixtures thereof, and intergrowths thereof.

11. The method of claim 9, wherein the oxygenate-containing feedstock is contacted with a silicoaluminophosphate catalyst at 200° C. to 700° C.

12. The method of claim 9, wherein the oxygenate-containing feedatock is contacted with a silicoaluminaphosphate catalyst in a reactor at an average gas superficial velocity of greater than 1 meter per second.

* * * * *